United States Patent [19]

Lerch et al.

[11] Patent Number: 6,018,095
[45] Date of Patent: Jan. 25, 2000

[54] METHOD FOR PREPARING AN IMPLANTABLE COMPOSITE MATERIAL, RESULTING MATERIAL, IMPLANT INCLUDING SAID MATERIAL, AND KIT THEREFOR

[75] Inventors: Alain Lerch, Toulouse; Patrick Frayssinet, Saint-Lys, both of France

[73] Assignee: Bioland, Toulouse, France

[21] Appl. No.: 08/983,562

[22] PCT Filed: Jun. 11, 1997

[86] PCT No.: PCT/FR97/01045

§ 371 Date: Jan. 22, 1998

§ 102(e) Date: Jan. 22, 1998

[87] PCT Pub. No.: WO97/47334

PCT Pub. Date: Dec. 18, 1997

[30] Foreign Application Priority Data

Jun. 14, 1996 [FR] France .................................. 96 07590

[51] Int. Cl.$^7$ ........................................................ A61F 2/28
[52] U.S. Cl. ................... 623/16; 623/11; 623/66
[58] Field of Search ................... 623/16, 11, 66; 128/897, 898; 433/167, 201.1; 501/1; 423/311

[56] References Cited

U.S. PATENT DOCUMENTS 4,626,392  12/1986  Kondo et al. .
4,976,746  12/1990  White et al. ............................. 623/16
5,091,344   2/1992  Enomoto et al. .
5,141,510   8/1992  Takagi et al. ............................. 623/16
5,769,897   6/1998  Harle ....................................... 623/16
5,820,632  10/1998  Constantz et al. ....................... 623/16

FOREIGN PATENT DOCUMENTS 0 360 244   3/1990   European Pat. Off. .
0 639 366   2/1995   European Pat. Off. .
43 02 072   7/1994   Germany .
3-242364   10/1991   Japan .

OTHER PUBLICATIONS

By P. Frayssinet et al., "Osseointegration of macroporous calcium phosphate ceramics having a different chemical composition", *Biomaterials*, 1993, vol. 14, No. 6.

Primary Examiner—Mickey Yu
Assistant Examiner—Dinh X. Nguyen
Attorney, Agent, or Firm—Young & Thompson

[57] ABSTRACT

A method for preparing a composite material for implantation into a biological medium, by preparing at least one block of solid porous matrix including at least one calcium salt; preparing a liquid solution hardenable into a solid composition including at least one calcium salt; dipping the matrix block into the liquid solution; and drying and hardening the liquid solution. The resulting composite material, an implant including the material, and a kit for extemporaneously carrying out the method, are also disclosed.

23 Claims, No Drawings

METHOD FOR PREPARING AN IMPLANTABLE COMPOSITE MATERIAL, RESULTING MATERIAL, IMPLANT INCLUDING SAID MATERIAL, AND KIT THEREFOR

BACKGROUND OF THE INVENTION

The invention relates to a method for preparing a solid composite material to be implanted in a human or animal biological medium, especially as a bone or dental substitute; a resulting material; an implant comprising such a material and a kit for carrying out said method extemporaneously.

In all the following specification of the present application, the term "implant" indicates any device, apparatus, mechanism, piece or group of pieces, of natural or artificial origin, organic or inorganic, in a solid condition, biocompatible and implantable in the human or animal body, excluding the fluid, pasty or divided compositions.

As examples of implants, bone, dental or maxillo-facial protheses, as well as filling, stopping or interface inserts, may be mentioned.

The use of porous ceramics having interconnected pores as an implantable solid material for bone substitutes was already described (see for ex ample EP-A-O 360 244 a nd "Osseointegration of macroporous calcium phosphate ceramic s having a different chemical composition", Frayssinet et al., Biomaterials 1993, Vol. 14, No 6, p 423–429). Due to their very macroporosity as such, the implantable biocompatible porous solid matrices such as ceramics, and more specifically the matrices having interconnected pores, are advantageous in that they increase the interchange surface area with the biological medium, are bioresorbable, promote the revascularization of the tissues and have excellent osteoconductive properties. Moreover, growth agents may be deposited into the pores by means of precipitation.

Such porous ceramics, however, are brittle and friable and are not able to be easily shaped by the practitioner during an operation. Further, the fixation of screws or pins in such ceramics is likewise impossible. Accordingly, the practical use of such ceramics is currently limited to the rare cases when it is certain, beforehand, that the material neither will have to be dressed again and adjusted extemporaneously, nor to support fixation screws.

Further, porous ceramics have a poor mechanical strength (2 to 4 MPa in compression), inadequate in a number of applications, for example when a renewed load of the application site is necessary before healing is completed.

Besides, implantable, biocompatible, phosphocalcic hydraulic cements are known (for example EP-A-0 639 366), i.e. hardenable pasty or fluid compositions allowing the realization of prosthetic assemblies or fillings during orthopaedic surgical operations. Although easily moldable by the practitioner, such cements cannot be used for realizing solid implants such as bone protheses having a predetermined general shape, which must resist from the moment of the implantation high stresses and/or wherein screws have to be screwed for the attachment of other elements or members. Accordingly, such cements are used only for cementing implants or members on each other, or sometimes as a filling material in sites which are not liable to undergo severe stresses.

SUMMARY OF THE INVENTION

In this connection, the invention aims at providing a composite material and the preparation method thereof, for the implantation in a biological medium (animal or human body), which has the advantages of the porous ceramics with interconnected pores (rapid and complete resorption, osteoconduction . . . ), but with improved mechanical properties.

The invention aims specifically at providing an implantable composite material able to be used in the composition of an implant, and which is able to be easily shaped, dressed, cut, drilled . . . , especiallly by the practitioner during the installation of the implant.

The invention also aims at providing such a material which is able to undergo stresses as early as the implantation.

The invention also aims at providing such a material wherein pins or screws such as self-drilling screws may be inserted and fixed, and which provides a good holding of such screws.

The invention also aims at providing an implantable composite material which is resorbable by a biological medium, and having a compression strength equivalent to that of the natural bone, particularly greater than 10 MPa, and more particularly in the range of 20 MPa.

The invention also aims at providing such a composite material having resorption kinetics in the biological medium able to be determined and adjusted before the implantation.

The invention also aims at providing a preparation method for such a composite material.

The invention also aims at providing a bone prothetic implant comprising a material having the above mentioned advantages.

The invention also aims at providing a preparation method of such an implant.

More specifically, the invention aims at providing a preparation method for a composite material and a method for the preparation of implants, especially of bone or dental substitutes, such methods being particularly simple, rapid and able to be carried out at least partially by the practitioner not long before the operation, or even during the operation.

In order to achieve these goals, the invention relates to a method for preparing a composite material to be implanted in a human or animal biological medium, characterized in that:

at least one block of a biocompatible porous solid matrix is selected or previously prepared, which is mainly comprised of at least one calcium salt selected from calcium phosphates, calcium sulfates and calcium carbonates, separate from the solid matrix, a hardenable liquid solution is prepared, which is adapted to form once hardened a hardened biocompatible solid composition mainly comprised of at least one calcium salt selected from calcium phosphates, calcium sulfates and calcium carbonates, and which is adapted to be entirely resorbable by the medium wherein the implant is to be implanted, the matrix block is immersed in the liquid solution before the hardening thereof, during a period which allows said solution to impregnate and fill the porous volume of the matrix block to the core, the liquid solution is then allowed to dry and harden into a solid composition.

According to the invention, each resulting block of composite material is then advantageously shaped.

According to the invention, at least one entirely porous block is prepared, and especially a macroporous block having a porosity which is preferably at least essentially uniform in the whole volume of the block.

The invention also relates to a composite material obtained with a method according to the invention. Accordingly, the invention relates to a composite material to be implanted in a human or animal biological medium, characterized in that it comprises:

a) a biocompatible porous solid matrix having a chemical composition which mainly contains at least one calcium salt selected from calcium phosphates, calcium sulfates and calcium carbonates, b) a biocompatible, undivided, compact, solid composition of a hardened hydraulic cement which is comprised of at least one calcium salt selected from calcium phosphates, calcium sulfates and calcium carbonates, said solid composition filling the porous volume and being adapted to be entirely resorbable by the medium wherein the implant is to be implanted.

According to the invention, the solid composition is advantageously selected to have a compress ion strength greater than 10 MPa, and especially in the range between 20 MPa and 50 MPa.

Further and according to the invention, the solid composition is advantageously selected to have a Young modulus in the range between 700 MPa and 1000 MPa.

More specifically and according to the invention, the solid composition is mainly comprised of dehydrated dicalcium phosphate $CaHPO_4.2H_2O$ (DCPD).

Further and according to the invention, the solid composition is advantageously of the type obtained by mixing a powdered β-tricalcium phosphate in an orthophosphoric acid solution which is allowed to harden at ambient temperature.

According to the invention, the matrix is also advantageously adapted to be entirely resorbable in said medium, and the solid composition is adapted to have a resorption kinetics in said medium quicker than that of the matrix; and the solid composition is adapted to be resorbable in said medium within a period shorter than three months, especially in the range of a few weeks.

According to the invention, the matrix is advantageously an inorganic, entirely porous matrix, especially a macroporous ceramic (i. e. having a porosity which is greater than the theoretical porosity thereof, having pores with an average size in the range of 50 μm and 2000 μm), and preferably having interconnected pores. The mean size of the pores is advantageously in the range between 200 μm and 500 μm.

According to the invention, the matrix advantageously has a porosity which is at least essentially uniform in the whole volume thereof, and which may be in the range between 5% and 85%, especially between 50% and 85%.

According to the invention, the matrix is advantageously selected to have a compression strength in the range between 1 MPa and 6 MPa and a Young modulus in the range between 10 MPa and 200 MPa.

According to the invention, the matrix advantageously contains a weight proportion X of hydroxyapatite (HAP) $Ca_{10}(PO_4)_6(OH)_2$, and a weight proportion Y of tricalcium phosphate $Ca_3(PO_4)_2$. According to the invention, the material is advantageously characterized in that X+Y=100%. For example and according to the invention, X is in the range of 75% and Y in the range of 25%.

According to the invention, the matrix and/or the solid composition (cement) advantageously incorporate at least one bioactive agent. By virtue of the invention, the in situ liberation kinetics of such a bioactive agent may be easily controlled, since it corresponds at least essentially to the resorption kinetics of the matrix and/or solid composition.

According to the invention, the matrix may be impregnated with a bioactive agent having liberation kinetics which must be slow, for example prolonged during several months, and the cement with a bioactive agent having liberation kinetics which must be quick, for example limited to a few weeks.

The invention also relates to an implant, and more specifically a bone or dental substitute which is characterized in that it comprises a material according to the invention.

Advantageously, an implant according to the invention is characterized in that it comprises at least a portion which is constituted of a material according to the invention, and which is to be placed in contact with a human or animal biological medium, especially a bone tissue.

The invention also relates to a kit for carrying out a method according to the invention extemporaneously, characterized in that it comprises at least one block of a biocompatible porous solid matrix and one dose of each of the constituents necessary to obtain said liquid solution which, when hardened, forms the biocompatible solid composition. The kit according to the invention comprises for example one block of calcium phosphate macroporous ceramic, one dose of powdered β-tricalcium phosphate with 2.5% of anhydrous sodium pyrophosphate, and one dose of an orthophosphoric acid solution with a concentration in the range between 1 and 5 mol/l, especially between 3.5 and 4.5 mol/l. The ratio of the weight (in grams) of the powder to the volume (in ml) of the dose of acid is in the range between 0.5 and 5, preferably between 1 and 2.

The invention also relates to a material, an implant, a method and a kit which comprise in combination all or a part of the characteristics mentioned above or below.

DETAILED DESCRIPTION OF THE INVENTION

The following description illustrates preparation examples of a material and an implant according to the invention.

EXAMPLES

Example 1

1) A barbotine comprising 1625 g of powdered hydroxyapatite and 875 g of powdered β-tricalcium phosphate, 45 g of a synthetic polyelectrolyte free from alkali (liquid dispersant), 30 g of powdered polyethylene oxide (organic binder), and 1165 ml of water, is prepared in a 15 l mixing vessel.

Cylinders with a diameter of 10 mm and a height of 10 mm of a polyurethane foam are immersed in this barbotine, and each foam cylinder is impregnated to the core by kneading until an impregnation ratio (ratio of the weight of barbotine to the weight of foam) of 25 is obtained.

The impregnated foam is placed in an oven at a temperature of 1150° C. during 15 min. once the oven is cold, a macroporous ceramic is obtained, the organic components being evaporated. Such ceramic has a porosity of 75%. Such a ceramic is known to be entirely resorbable in a biological medium within approximately 18 months.

The compression strength of the ceramic is measured through submitting a cylinder with a diameter of 10 mm and a height of 10 mm to a compression test. The compression strength is 1 MPa and the Young modulus is 20 MPa.

2) A powdered β-tricalcium phosphate (TCP) is prepared by reacting hydroxyapatite and dihydrated dicalcium phosphate at 1150° C. during 180 min.

2.954 g of TCP are mixed with 0.046 g of powdered anhydrous sodium pyrophosphate.

These 3 g of powder are poured in 2.3 ml of an aqueous solution of orthophosphoric acid 4 M and sulfuric acid 0.1 M.

After reacting from 30 s to 1 min, a uniform mixture of hardenable liquid solution is obtained.

3) 4 cylinders of the macroporous ceramic prepared as in 1) are immersed in this hardenable liquid solution during a period in the range of 20 s until every air bubble has been expelled from the pores.

4) The impregnated cylinders are removed from the solution and allowed to dry freely in the air. A hardening of the solution is observed within approximately 5 min, into a solid, compact, undivided composition which fills the porous volume of the ceramic.

Five days later (evaporation of the water), compression tests are realized. The resulting compression strength is 15 MPa and the Young modulus is 400 MPa.

5) The cylinders appear to be able to be cut with a saw, while displaying a perfect surface condition.

A pre-bore hole is drilled in one cylinder, and an osteosynthesis screw is screwed into this pre-bore hole by means of a screwdriver. The material appears to maintain the cohesion thereof and is not damaged, particularly around the screw which is perfectly held in place.

6) The hardenable solution obtained in 2) is used to prepare cylinders with a diameter of 5 mm and a height of 10 mm, which are implanted in the condyles of a series of 12 rabbits.

The rabbits are sacrificed the 15th day and the 6th, the 10th, and the 16th weeks after implantation, and the implantation sites were histologically examined.

It was established that during the first two weeks, an apposition of bone trabeculae occurs at the surface of the implant. Grains of material are found in the stomal tissue between the trabeculae as well as in the newly formed trabeculae.

At the sixth and ninth weeks, the cylinders are divided and bone trabeculae have penetrated the whole volume of the cylinders around the fragments. These fragments are in contact with the newly formed bone tissue, without any fibrous interposition. A great number of fragments are in the course of being wholly integrated into the bone tissue.

At the thirteenth week, the fragmentation process is enhanced, as well as that of bone integration. More than half of the implant volume has disappeared at that time.

As a conclusion, the solid composition permeating pores is entirely resorbable in a biological medium and has resorption kinetics quicker than the matrix.

Example 2

1) A barbotine comprising 1625 g of powdered hydroxyapatite and 875 g of β-tricalcium phosphate, 45 g of a synthetic polyelectrolyte free from alkali (liquid dispersant), 30 g of powdered polyethylene oxide (organic binder), and 1165 ml of water, is prepared in a 15 l mixing vessel.

Cylinders with a diameter of 10 mm and a height of 10 mm of a polyurethane foam are immersed in this barbotine, and each foam cylinder is impregnated to the core by kneading until an impregnation ratio (ratio of the weight of barbotine to the weight of foam) of 30 is obtained.

The impregnated foam is placed in an oven at a temperature of 1150° C. during 15 min. Once the oven is cold, a macroporous ceramic is obtained, the organic components being evaporated. Such ceramic has a porosity of 68%.

The compression strength of the ceramic is measured through submitting a cylinder with a diameter of 10 mm and a height of 10 mm to a compression test. The compression strength is 3 MPa and the Young modulus is 80 MPa.

Following the same steps 2), 3) and 4) as in Example 1, a composite material according to the invention is prepared. The same tests and studies as those mentioned under 4) and 5) in Example 1 are carried out with the same results on the composite material obtained in Example 2. After five days (evaporation of the water), compression tests are carried out. The resulting compression strength obtained is 20 MPa, and the Young modulus is 500 MPa.

Example 3

A composite material according to the invention is prepared as in Example 2 from a macroporous matrix of calcium phosphate comprised of 75 (weight) % of hydroxyapatite and 25 (weight) % of β-tricalcium phosphate. The porosity of such matrix is of 70% and the measured average size of the pores is of 500 μm. All the pores are interconnected. The matrix is immersed in a hardenable liquid solution of DCPD.

The composite material obtained after hardening is formed of cylinders with a diameter of 8 mm and a length of 15 mm, which are implanted in 9 mm boreholes drilled in the external condyles of 12 sheep. In each animal, one cylinder of composite material according to the invention is implanted in the femoral condyle, and one cylinder of the same size, formed only of the macroporous ceramic matrix of calcium phosphate used to prepare the composite material according to the invention, i. e. such matrix as obtained before immersion in the hardenable liquid solution, is implanted in the other condyle.

Four sheep are successively sacrificed the 20th, the 60th, and the 120th days after implantation, and the implantation sites are histologically examined.

After 20 days, none of the implants was osteointegrated. A few bone tissue trabeculae are formed in the tissue surrounding the implants. Such trabeculae originate generally from the sides of the cavity in the bone and extend towards the implant. The pores of the implants formed of the matrix only are invaded by fibrous tissue, and some trabeculae are found which are in contact with the external surface of the ceramic matrix.

Concerning the cylinders in composite material according to the invention, the bone trabeculae are often formed at the surface of the implant and some are imbedded in the cement which shows traces of damage in these zones. Some grains having a size of a few microns were eliminated, with resulting voids in the cemented pores wherein an extracellular matrix has formed. Those grains were phagocyted by mononucleated macrophages at the periphery of the implant.

The 60th day, the implants of matrix only are integrated in part with some bone growth at the surface of the external pores. The central portion of the matrix still contains fibrous tissue wherein mononucleated cells containing ceramic particles are visible.

Concerning the implants of composite material according to the invention, a gradual growth of bone tissue is observed in the external pores wherein the cement was slowly replaced by bone tissue. Most cement crystallites near the surface are coated with a proteic substance. These crystallites were phagocyted and degraded by the macrophages. A number of osteoblasts are distinguished at the surface of the inorganic aggregates. The localization of the osteoblasts at the surface seems to evidence a preferential differentiation process. Not all cement fragments were degraded by the macrophages. Some are embedded in the bone matrix which formed in the pores. Some extent of damage to the ceramic matrix is also observed.

The 120th day, a bone tissue growth in all cylinders was observed, together with a major degradation. No cement is anymore contained in any of the pores in the implants comprised of a material according to the invention, the cement being found in the inorganic particles in the macrophages. Some islets of macrophages are present in the bone marrow of the bone tissue. Islets of macrophages have phagocyted the bone tissue, but no exaggerated bone resorption could be established in the near vicinity of the implants.

On the contrary, the implants comprised of matrix only are totally integrated and show signs of resorption.

Histomorphometric measurements indicate that the bone quantity and the degree of ossification are higher in the implants of composite material according to the invention than in the implants formed of porous ceramic matrix only.

These tests demonstrate that the formation of a bone tissue at the surface of the material according to the invention is preceded by a deposit of a matrix of proteins, which deposit may sometimes not be associated with a synthesis by osteogenic cells in the immediate vicinity. Such matrix which penetrated the micropores of the material was not mineralized and seemed to be a prerequisite to the bone formation by the osteoblasts.

The bone formation process is very active in the cement degradation zones. The presence of the macrophages having phagocyted the calcium phosphate crystals did not trigger the activation of the osteoblasts, as evidenced by the absence of osteolysis of the bone tissue which invaded the ceramic. Moreover, it seems that the bone formation was increased by the presence of the cement, no clear explanation being given of this phenomenon. One possible explanation would be that such phenomenon is associated with the calcium phosphate cement degradation. The complexity of the macrophages activation and the large number of products these cells are able to synthesize could also explain these results in part.

As a conclusion, the composite material according to the invention has improved mechanical as well as biological properties.

We claim:

1. Method for preparing a composite material to be implanted in a human or animal biological medium, which comprises:
    selecting or preparing at least one block of a biocompatible porous solid matrix, said matrix being mainly comprised of at least one calcium salt selected from the group consisting of calcium phosphates, calcium sulfates and calcium carbonates;
    preparing a hardenable liquid solution separate from said solid matrix, said hardenable liquid solution being adapted to form, once hardened, a hardened biocompatible solid composition mainly comprised of at least one calcium salt selected from the group consisting of calcium phosphates, calcium sulfates and calcium carbonates, and which is adapted to be entirely resorbable by the medium where the implant is to be implanted;
    immersing the matrix block in said liquid solution before the hardening thereof, for a period which allows said solution to impregnate and fill the porous volume of said matrix block to the core; and
    allowing the liquid solution to dry and harden into a solid composition without sintering.

2. The method according to claim 1, further comprising shaping each resulting block of composite material.

3. The method according to claim 1, wherein said biocompatible porous solid matrix has interconnected pores.

4. A composite material to be implanted in a human or animal biological medium, and obtained by a method according to claim 1, the composite material comprising:
    a) a biocompatible porous solid matrix having a chemical composition which mainly contains at least one calcium salt selected from the group consisting of calcium phosphates, calcium sulfates and calcium carbonates;
    b) a biocompatible, undivided, compact, solid composition of a non-sintered hardened hydraulic cement which is comprised of at least one calcium salt selected from the group consisting of calcium phosphates, calcium sulfates and calcium carbonates, said solid composition filling the porous volume and being adapted to be entirely resorbable by the medium where the implant is to be implanted.

5. The composite material according to claim 4, wherein the solid composition is selected to have a compression strength greater than 10 MPa.

6. The composite material according to claim 5, wherein the compression strength ranges between 20 MPa and 50 MPa.

7. The composite material according to claim 4, wherein the solid composition is selected to have a Young modulus in the range between 700 MPa and 1000 MPa.

8. The composite material according to claim 4, wherein the solid composition is mainly comprised of dihydrated dicalcium phosphate $CaHPO_4.2H_2O$.

9. The composite material according to claim 4, wherein the solid composition is obtained by mixing a powdered β-tricalcium phosphate in an orthophosphoric acid solution.

10. The composite material according to claim 4, wherein the matrix is adapted to be entirely resorbable in said medium, and the solid composition is adapted to have a resorption kinetics in said medium quicker than said matrix.

11. The composite material according to claim 4, wherein the solid composition is adapted to be resorbable in said medium within a period shorter than three months.

12. The composite material according to claim 4, wherein the matrix is a macroporous ceramic.

13. The composite material according to claim 12, wherein the matrix has interconnected pores.

14. The composite material according to claim 4, wherein the matrix has a porosity ranging between 5% and 85%.

15. The composite material according to claim 4, wherein the matrix is selected to have a compression strength ranging between 1 MPa and 6 MPa.

16. The composite material according to claim 4, wherein the matrix is selected to have a Young modulus ranging between 10 MPa and 200 MPa.

17. The composite material according to claim 4, wherein the matrix contains a weight proportion X of hydroxyapatite $Ca_{10}(PO_4)_6(OH)_2$, and a weight proportion Y of tricalcium phosphate $Ca_3(PO_4)_2$.

18. The composite material according to claim 17, wherein X+Y=100%.

19. The composite material according to claim 18, wherein X is about 75% and Y is about 25%.

20. An implant comprising a composite material according to claim 4.

21. An implant comprising at least a portion in a composite material according to claim 4, which is to be placed in contact with a human or animal bone tissue.

22. Kit for carrying out extemporaneously a method according to claim 1, the kit comprising at least one block of a biocompatible porous solid matrix and on e dose of each constituent necessary to obtain the liquid solution which forms the biocompatible solid composition.

23. The kit according to claim 22, comprising one block of calcium phosphate macroporous ceramic, one dose of powdered β-tricalcium phosphate with 2.5% of anhydrous sodium pyrophosphate, and one dose of orthophosphoric acid solution having a concentration ranging between 1 and 5 mol/l.

* * * * *